United States Patent
Smith

(10) Patent No.: US 11,510,014 B2
(45) Date of Patent: *Nov. 22, 2022

(54) DYNAMIC STIMULUS RESOLUTION ADAPTION

(71) Applicant: Cochlear Limited, Macquarie University (AU)

(72) Inventor: Zachary Mark Smith, Pymble (AU)

(73) Assignee: Cochlear Limited, Macquarie University (AU)

( * ) Notice: Subject to any disclaimer, the term of this patent is extended or adjusted under 35 U.S.C. 154(b) by 0 days.

This patent is subject to a terminal disclaimer.

(21) Appl. No.: 16/929,434

(22) Filed: Jul. 15, 2020

(65) Prior Publication Data

US 2020/0382878 A1 Dec. 3, 2020

Related U.S. Application Data

(63) Continuation of application No. 15/358,225, filed on Nov. 22, 2016, now Pat. No. 10,743,114.

(51) Int. Cl.
*A61N 1/36* (2006.01)
*H04R 25/00* (2006.01)
*A61N 1/05* (2006.01)

(52) U.S. Cl.
CPC ....... *H04R 25/305* (2013.01); *A61N 1/36036* (2017.08); *A61N 1/36038* (2017.08);
(Continued)

(58) Field of Classification Search
CPC .................. A61N 1/36039; H04R 2225/41
See application file for complete search history.

(56) References Cited

U.S. PATENT DOCUMENTS

| | | | | |
|---|---|---|---|---|
| 4,532,930 A | * | 8/1985 | Crosby | A61N 1/36038 607/57 |
| 6,068,652 A | * | 5/2000 | Cohen | A61N 1/36038 607/57 |

(Continued)

FOREIGN PATENT DOCUMENTS

| | | |
|---|---|---|
| KR | 100859979 B1 | 9/2008 |
| WO | 2014135203 A1 | 9/2014 |

OTHER PUBLICATIONS

International Search Report and Written Opinion in corresponding International Application No. PCT/IB2017/056964, dated Feb. 13, 2018, 13 pgs.

(Continued)

*Primary Examiner* — Eric D. Bertram
(74) *Attorney, Agent, or Firm* — Edell, Shapiro & Finnan, LLC

(57) ABSTRACT

Presented herein are techniques that use acoustic scene (environmental) analysis to determine the sound class of sound signals received at a hearing prosthesis and, accordingly, assess the estimated listening difficulty that the acoustic environment presents to a recipient of the hearing prosthesis. This difficulty of the recipient's listening situation can be used to adjust, adapt, or otherwise set the resolution of the electrical stimulation signals delivered to the recipient to evoke perception of the sound signals. In other words, the resolution of the electrical stimulation signals is dynamically adapted based on the present acoustic environment of the hearing prosthesis.

20 Claims, 10 Drawing Sheets

(52) U.S. Cl.
CPC ........ *A61N 1/36039* (2017.08); *A61N 1/0541* (2013.01); *H04R 2225/41* (2013.01); *H04R 2225/67* (2013.01)

(56) References Cited

U.S. PATENT DOCUMENTS

| | | | |
|---|---|---|---|
| 6,611,717 B1* | 8/2003 | Clark | A61N 1/36038 607/56 |
| 7,103,417 B1* | 9/2006 | Segel | A61N 1/36038 607/57 |
| 7,889,879 B2 | 2/2011 | Dillon | |
| 8,000,797 B1* | 8/2011 | Sarpeshkar | A61N 1/36185 607/57 |
| 8,914,124 B2 | 12/2014 | Litvak et al. | |
| 9,446,236 B2 | 9/2016 | Litvak | |
| 9,511,225 B2 | 12/2016 | Milczynski et al. | |
| 10,743,114 B2* | 8/2020 | Smith | A61N 1/36036 |
| 2005/0222644 A1 | 10/2005 | Killian | |
| 2006/0025833 A1* | 2/2006 | Daly | A61N 1/36038 607/55 |
| 2006/0190059 A1* | 8/2006 | Griffith | A61N 1/37229 607/57 |
| 2007/0032838 A1* | 2/2007 | Seligman | H02J 7/007182 607/55 |
| 2011/0081033 A1* | 4/2011 | Kitazawa | A61B 5/121 381/321 |
| 2011/0093038 A1 | 4/2011 | Honert | |
| 2011/0230933 A1* | 9/2011 | Choi | A61N 1/36038 607/56 |
| 2011/0286618 A1 | 11/2011 | Vandali | |
| 2011/0288613 A1 | 11/2011 | Smith et al. | |
| 2013/0023967 A1 | 1/2013 | Stafford | |
| 2013/0218237 A1* | 8/2013 | Svirsky | A61N 1/36039 607/57 |
| 2013/0282070 A1* | 10/2013 | Cowan | A61N 1/37217 607/3 |
| 2014/0005746 A1 | 1/2014 | Schleich et al. | |
| 2014/0105433 A1* | 4/2014 | Goorevich | H04R 25/505 381/312 |
| 2014/0172042 A1 | 6/2014 | Goorevich | |
| 2014/0198922 A1* | 7/2014 | Mauger | H04R 25/00 381/60 |
| 2015/0246230 A1* | 9/2015 | Litvak | H04R 25/606 607/57 |
| 2015/0328457 A1 | 11/2015 | Litvak et al. | |
| 2015/0374988 A1 | 12/2015 | Laudanski | |
| 2016/0144178 A1 | 5/2016 | Hillbratt | |
| 2016/0184586 A1 | 6/2016 | Okuyama | |
| 2017/0340876 A1* | 11/2017 | Vanpoucke | A61N 1/36038 |

OTHER PUBLICATIONS

Extended European Search Report received in application No. 17873277.2, dated Apr. 24, 2020, (7 pages).

* cited by examiner

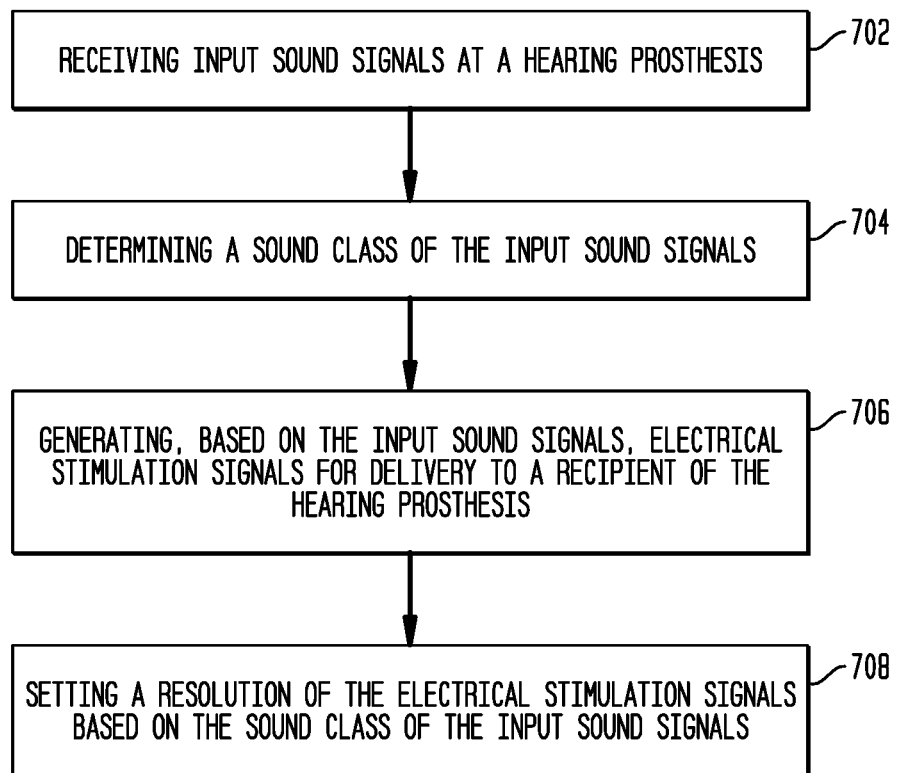

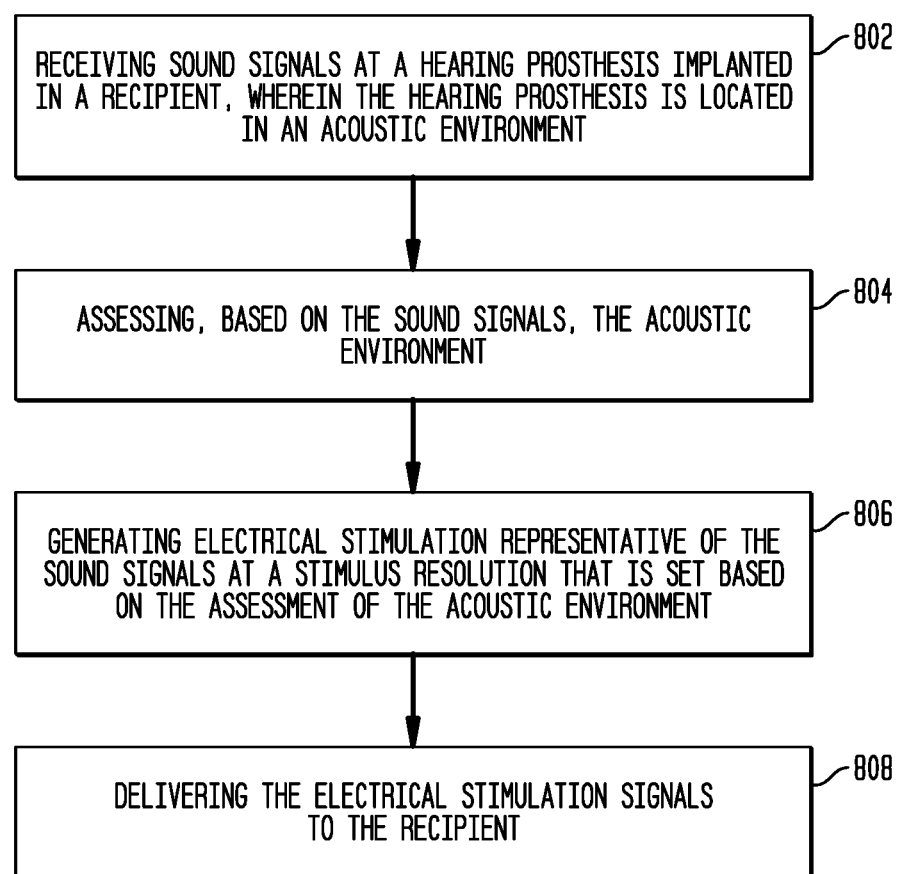

DYNAMIC STIMULUS RESOLUTION ADAPTION

CROSS REFERENCE TO RELATED APPLICATIONS

This application is a continuation of U.S. application Ser. No. 15/358,225, now U.S. Pat. No. 10,743,114, filed on Nov. 22, 2016, the contents of which are hereby incorporated in their entirety.

BACKGROUND

Field of the Invention

The present invention relates generally to electrically-stimulating hearing prostheses.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. An auditory brainstem stimulator is another type of stimulating auditory prosthesis that might also be proposed when a recipient experiences sensorineural hearing loss due to damage to the auditory nerve.

Certain individuals suffer from only partial sensorineural hearing loss and, as such, retain at least some residual hearing. These individuals may be candidates for electro-acoustic hearing prostheses.

SUMMARY

In one aspect, a method is provided. The method comprises: receiving input sound signals at a hearing prosthesis; determining a sound class of the input sound signals; generating, based on the input sound signals, electrical stimulation signals for delivery to a recipient of the hearing prosthesis; and setting a resolution of the electrical stimulation signals based on the sound class of the input sound signals.

In another aspect, a method is provided. The method comprises: receiving sound signals at a hearing prosthesis located in an acoustic environment; assessing, based on the sound signals, the acoustic environment; generating electrical stimulation representative of the sound signals at a stimulus resolution that is set based on the assessment of the acoustic environment; and delivering the electrical stimulation signals to the recipient.

In another aspect, a hearing prosthesis is provided. The hearing prosthesis comprises: one or more sound input elements configured to receive sound signals; a sound processing path configured to convert the sound signals into one or more output signals for use in delivering electrical stimulation to a recipient; and a stimulus resolution adaption module configured to set a resolution of the electrical stimulation based on a sound class of the sound signals.

BRIEF DESCRIPTION OF THE DRAWINGS

Embodiments of the present invention are described herein in conjunction with the accompanying drawings, in which:

FIG. 7 is a flowchart of a method in accordance with embodiments presented herein; and FIG. 8 is a flowchart of another method in accordance with embodiments presented herein.

DETAILED DESCRIPTION

Embodiments of the present invention are generally directed to the use of acoustic scene (environmental) analysis to determine the sound class of sound signals received at a hearing prosthesis and, accordingly, assess the estimated listening difficulty that the acoustic environment presents to a recipient of the hearing prosthesis. This difficulty of the recipient's listening situation can be used to adjust, adapt, or otherwise set the resolution (e.g., through multipolar widening and/or focusing) of the electrical stimulation signals delivered to the recipient to evoke perception of the sound signals. In other words, the resolution of the electrical stimulation signals is dynamically adapted based on the present acoustic environment of the hearing prosthesis. This dynamic adaption of the stimulation resolution may optimize the tradeoff between power consumption and hearing performance.

There are a number of different types of hearing prostheses in which embodiments of the present invention may be implemented. However, merely for ease of illustration, the techniques presented herein are primarily described with reference to one type of hearing prosthesis, namely a cochlear implant. However, it is to be appreciated that the techniques presented herein may be used in other hearing prostheses, such as auditory brainstem stimulators, electro-acoustic hearing prostheses, bimodal hearing prostheses, etc.

Figure 1A:
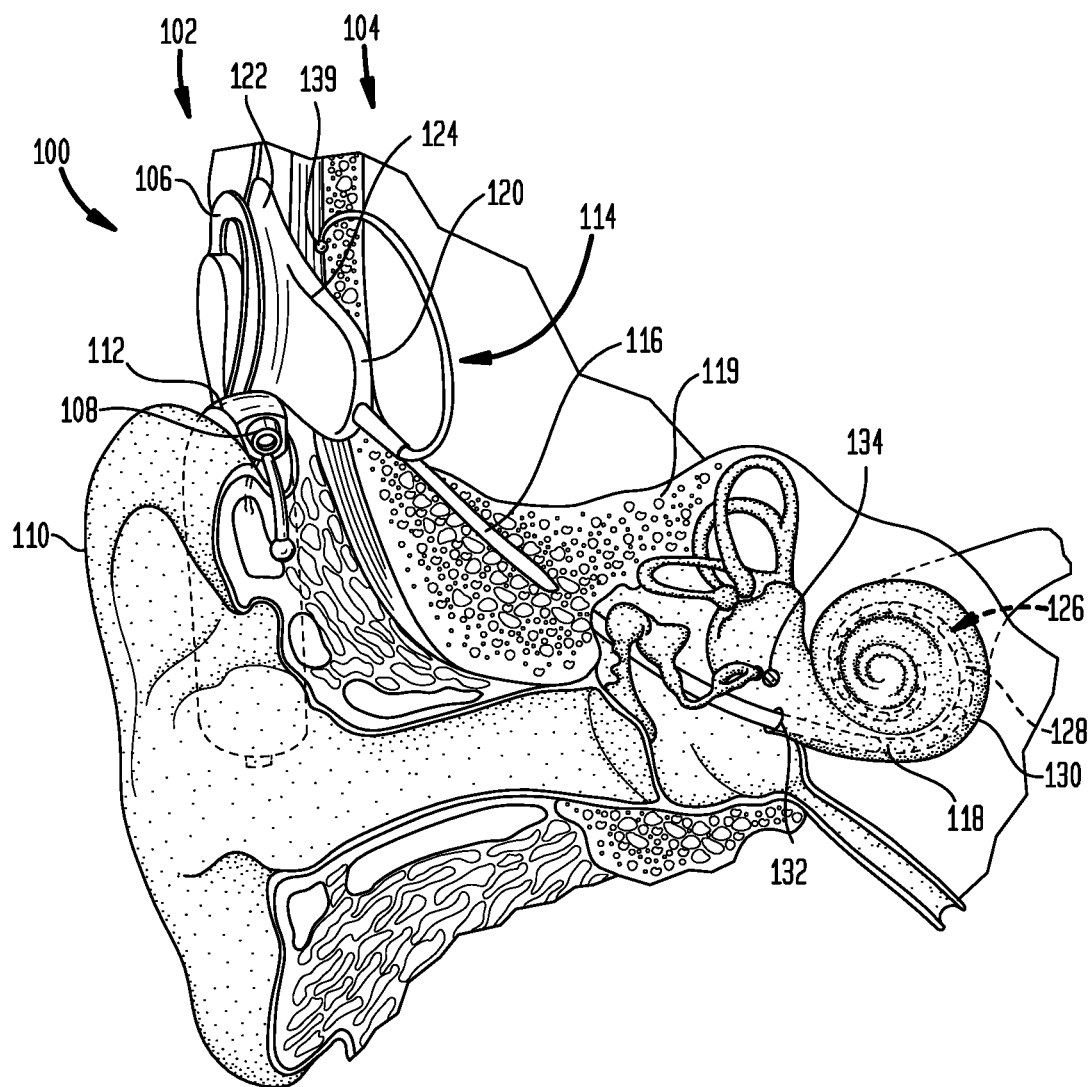
FIG. 1A is a schematic diagram illustrating a cochlear implant system in accordance with embodiments presented herein.

FIG. 1A is a schematic diagram of an exemplary cochlear implant 100 configured to implement embodiments of the present invention. The cochlear implant 100 comprises an external component 102 and an internal/implantable component 104.

The external component 102 is directly or indirectly attached to the body of the recipient and typically comprises an external coil 106 and, generally, a magnet (not shown in FIG. 1A) fixed relative to the external coil 106. The external component 102 also comprises one or more sound input elements 108 (e.g., microphones, telecoils, etc.) for detecting/receiving input sound signals, and a sound processing unit 112. The sound processing unit 112 includes, for example, one or more batteries (not shown in FIG. 1A) and a sound processor (also not shown in FIG. 1A). The sound processor is configured to process electrical signals generated by a sound input element 108 that is positioned, in the depicted embodiment, by auricle 110 of the recipient. The sound processor provides the processed signals to external coil 106 via, for example, a cable (not shown in FIG. 1A).

The implantable component 104 comprises an implant body 114, a lead region 116, and an elongate intra-cochlear stimulating assembly 118. The implant body 114 comprises a stimulator unit 120, an internal/implantable coil 122, and an internal receiver/transceiver unit 124, sometimes referred to herein as transceiver unit 124. The transceiver unit 124 is connected to the implantable coil 122 and, generally, a magnet (not shown) fixed relative to the internal coil 122.

The magnets in the external component 102 and implantable component 104 facilitate the operational alignment of the external coil 106 with the implantable coil 122. The operational alignment of the coils enables the implantable coil 122 to transmit/receive power and data to/from the external coil 106. More specifically, in certain examples, external coil 106 transmits electrical signals (e.g., power and stimulation data) to implantable coil 122 via a radio frequency (RF) link. Implantable coil 122 is typically a wire antenna coil comprised of multiple turns of electrically insulated single-strand or multi-strand platinum or gold wire. The electrical insulation of implantable coil 122 is provided by a flexible molding (e.g., silicone molding). In use, transceiver unit 124 may be positioned in a recess of the temporal bone of the recipient. Various other types of energy transfer, such as infrared (IR), electromagnetic, capacitive and inductive transfer, may be used to transfer the power and/or data from an external device to a cochlear implant and, as such, FIG. 1A illustrates only one example arrangement.

Elongate stimulating assembly 118 is configured to be at least partially implanted in cochlea 130 and includes a plurality of longitudinally spaced intra-cochlear electrical stimulating contacts (electrodes) 128 that collectively form a contact array 126. Stimulating assembly 118 extends through an opening in the cochlea 130 (e.g., cochleostomy 132, the round window 134, etc.) and has a proximal end connected to stimulator unit 120 via lead region 116 that extends through mastoid bone 119. Lead region 116 couples the stimulating assembly 118 to implant body 114 and, more particularly, stimulator unit 120.

In general, the sound processor in sound processing unit 112 is configured to execute sound processing and coding to convert a detected sound into a coded signal that represents the detected sound signals. These encoded data are sometimes referred to herein as processed sound signals and are sent to the implantable component 104. The stimulator unit 120 is configured to utilize the processed sound signals to generate electrical stimulation signals that are delivered to the recipient's cochlea via one or more stimulation channels. In this way, cochlear implant stimulates the recipient's auditory nerve cells, bypassing absent or defective hair cells that normally transduce acoustic vibrations into neural activity.

Figure 1B:
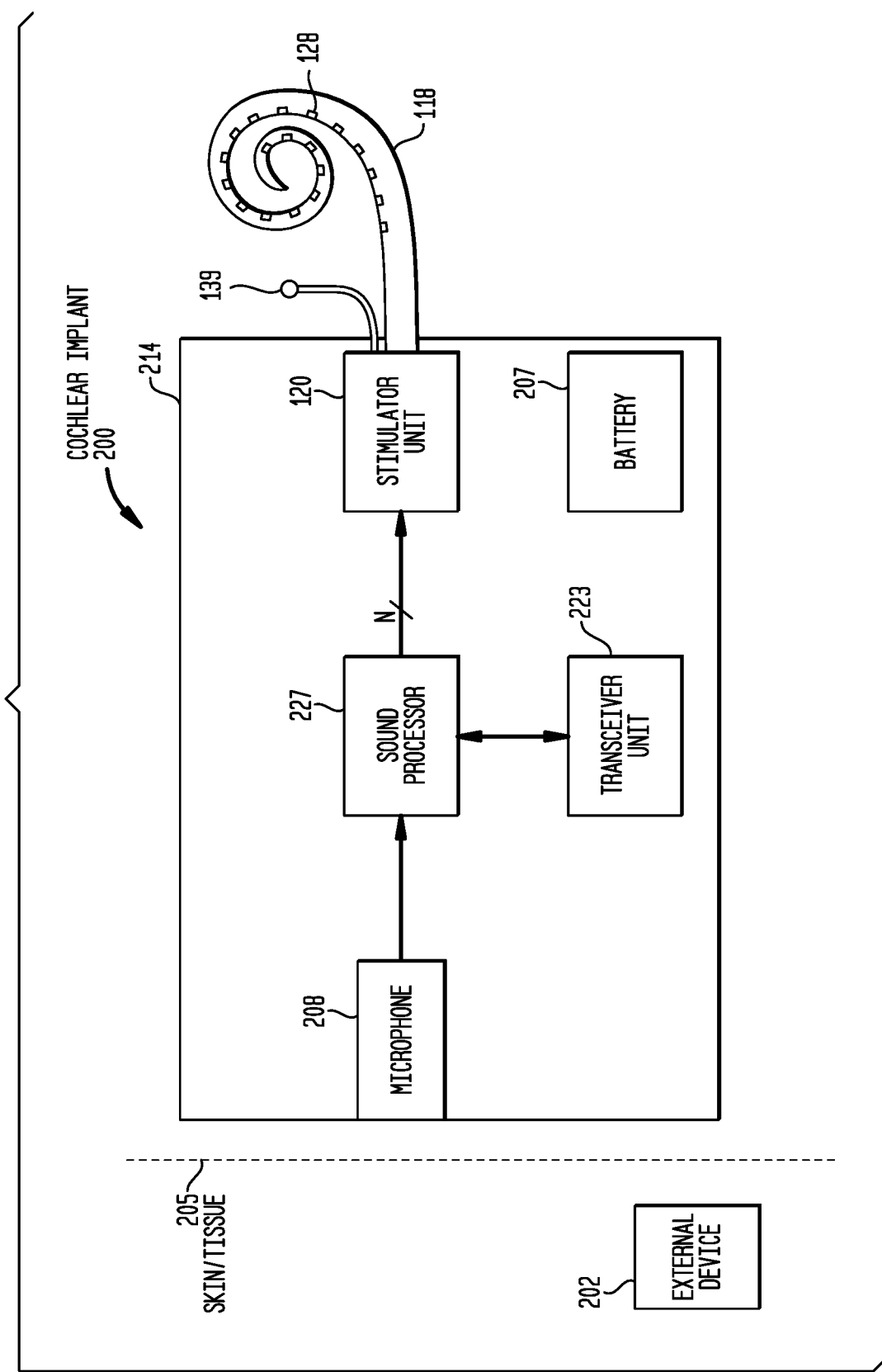
FIG. 1B is a block diagram of a totally implantable cochlear implant system in accordance with embodiments presented herein.

FIG. 1A illustrates an arrangement in which the cochlear implant 100 includes an external component. However, it is to be appreciated that embodiments of the present invention may be implemented in cochlear implant systems having alternative arrangements. For example, FIG. 1B is a functional block diagram of an exemplary totally implantable cochlear implant 200 configured to implement embodiments of the present invention. Since the cochlear implant 200 is totally implantable, all components of cochlear implant 200 are configured to be implanted under skin/tissue 205 of a recipient. Because all components are implantable, cochlear implant 200 operates, for at least a finite period of time, without the need of an external device. An external device 202 can be used to, for example, charge the internal power source (battery) 207. External device 202 may be a dedicated charger or a conventional cochlear implant sound processor.

Cochlear implant 200 includes an implant body (main implantable component) 214 and an implantable microphone 208, an elongate intra-cochlear stimulating assembly 118 as described above with reference to FIG. 1A. The microphone 208 may be disposed in, or electrically connected to, the implant body 214. The implant body 214 further comprises an internal transceiver unit 223, a sound processor 227, a stimulator unit 120 as described with reference to FIG. 1A, and the battery 207.

The sound processor 227 is configured to execute sound processing and coding to convert received/detected sound signals (e.g., received by microphone 208) into processed sound signals.

The transceiver unit 223 permits cochlear implant 200 to receive and/or transmit signals to external device 202. For example, transceiver unit 223 may be configured to transcutaneously receive power and/or data from external device 202. However, as used herein, transceiver unit 223 refers to any collection of one or more implanted components which form part of a transcutaneous energy transfer system. Further, transceiver unit 223 includes any number of component(s) which receive and/or transmit data or power, such as, for example a coil for a magnetic inductive arrangement, an antenna for an alternative RF system, capacitive plates, or any other suitable arrangement.

As noted above, FIG. 1A illustrates an embodiment in which the external component 102 includes the sound processor. As such, in the illustrative arrangement of FIG. 1A, processed sound signals are provided to the implanted stimulator unit 120 via the RF link between the external coil 106 and the internal coil 122. However, in the embodiment of FIG. 1B, the sound processor 227 is implanted in the recipient. As such, in the embodiments of FIG. 1B, the processed sound signals do not traverse the RF link, but instead are provided directly to the stimulator unit 120.

The human auditory system is composed of many structural components, some of which are connected extensively by bundles of nerve cells (neurons). Each nerve cell has a cell membrane which acts as a barrier to prevent intercellular fluid from mixing with extracellular fluid. The intercellular and extracellular fluids have different concentrations of ions, which leads to a difference in charge between the fluids. This difference in charge across the cell membrane is referred to herein as the membrane potential (Vm) of the nerve cell. Nerve cells use membrane potentials to transmit signals between different parts of the auditory system.

In nerve cells that are at rest (i.e., not transmitting a nerve signal) the membrane potential is referred to as the resting potential of the nerve cell. Upon receipt of a stimulus, the electrical properties of a nerve cell membrane are subjected to abrupt changes, referred to herein as a nerve action potential, or simply action potential. The action potential represents the transient depolarization and repolarization of the nerve cell membrane. The action potential causes electrical signal transmission along the conductive core (axon) of a nerve cell. Signals may be then transmitted along a group of nerve cells via such propagating action potentials.

Figure 2:
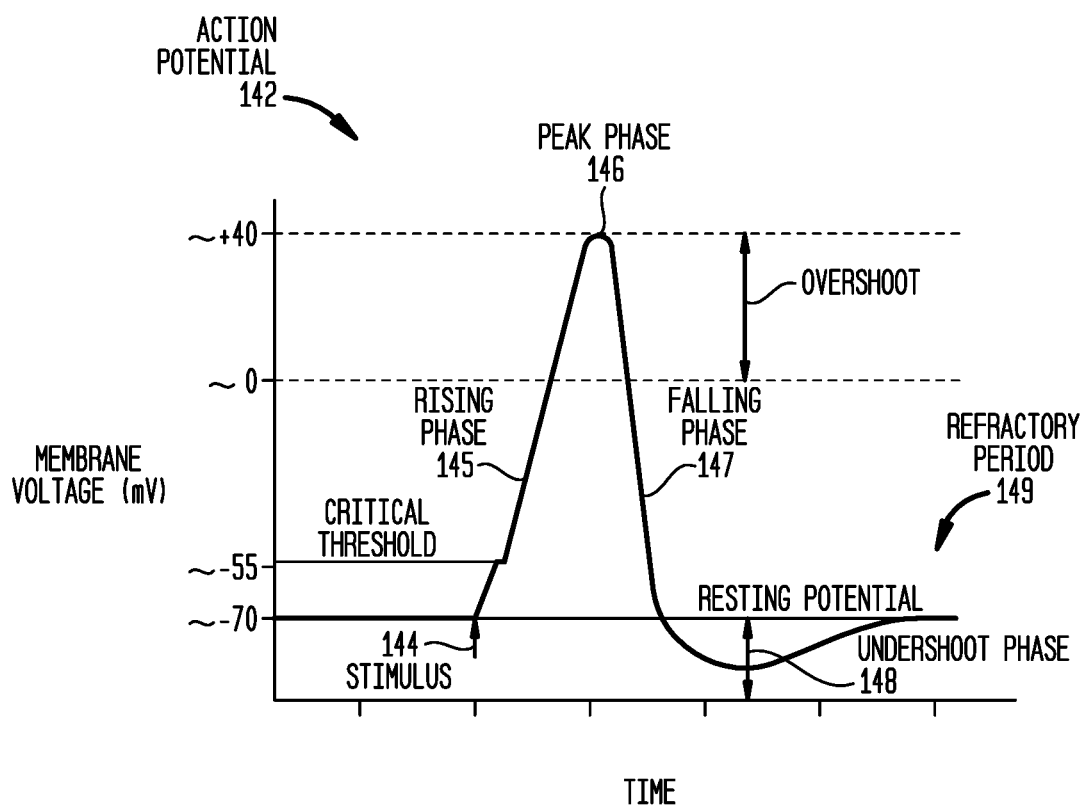
FIG. 2 is a graph illustrating various phases of an idealized action potential as the potential passes through a nerve cell.

FIG. 2 illustrates various phases of an idealized action potential 142 as the potential passes through a nerve cell. The action potential is presented as membrane voltage in millivolts (mV) versus time. The membrane voltages and times shown in FIG. 2 are for illustration purposes only and the actual values may vary depending on the individual. Prior to application of a stimulus 144 to the nerve cell, the resting potential of the nerve cell is approximately −70 mV. Stimulus 144 is applied at a first time. In normal hearing, this stimulus is provided by movement of the hair cells of the cochlea. Movement of these hair cells results in the release of neurotransmitter into the synaptic cleft, which in return leads to action potentials in individual auditory nerve fibers. In cochlear implants, the stimulus 144 is an electrical stimulation signal (electrical stimulation).

Following application of stimulus 144, the nerve cell begins to depolarize. Depolarization of the nerve cell refers to the fact that the voltage of the cell becomes more positive following stimulus 144. When the membrane of the nerve cell becomes depolarized beyond the cell's critical threshold, the nerve cell undergoes an action potential. This action potential is sometimes referred to as the "firing" or "activation" of the nerve cell. As used herein, the critical threshold of a nerve cell, group of nerve cells, etc. refers to the threshold level at which the nerve cell, group of nerve cells, etc. will undergo an action potential. In the example illustrated in FIG. 2, the critical threshold level for firing of the nerve cell is approximately −50 mV. The critical threshold and other transitions may be different for various recipients and so the values provided in FIG. 2 are merely illustrative.

The course of the illustrative action potential in the nerve cell can be generally divided into five phases. These five phases are shown in FIG. 2 as a rising phase 145, a peak phase 146, a falling phase 147, an undershoot phase 148, and finally a refractory phase (period) 149. During rising phase 145, the membrane voltage continues to depolarize and the point at which depolarization ceases is shown as peak phase 146. In the example of FIG. 2, at this peak phase 146, the membrane voltage reaches a maximum value of approximately 40 mV.

Following peak phase 146, the action potential undergoes falling phase 147. During falling phase 147, the membrane voltage becomes increasingly more negative, sometimes referred to as hyperpolarization of the nerve cell. This hyperpolarization causes the membrane voltage to temporarily become more negatively charged than when the nerve cell is at rest. This phase is referred to as the undershoot phase 148 of action potential 142. Following this undershoot phase 148, there is a time period during which it is impossible or difficult for the nerve cells to fire. This time period is referred to as the refractory phase (period) 149.

As noted above, the nerve cell must obtain a membrane voltage above a critical threshold before the nerve cell may fire/activate. The number of nerve cells that fire in response to electrical stimulation (current) can affect the "resolution" of the electrical stimulation. As used herein, the resolution of the electrical stimulation or the "stimulus resolution" refers to the amount of acoustic detail (i.e., the spectral and/or temporal detail from the input acoustic sound signal(s)) that is delivered by the electrical stimulation at the implanted electrodes in the cochlea and, in turn, received by the primary auditory neurons (spiral ganglion cells). As described further below, electrical stimulation has a number of characteristics/attributes that control the stimulus resolution. These attributes include for example, the spatial attributes of the electrical stimulation, temporal attributes of the electrical stimulation, frequency attributes of the electrical stimulation, instantaneous spectral bandwidth attributes of the electrical stimulation, etc. The spatial attributes of the electrical stimulation control the width along the frequency axis (i.e., along the basilar membrane) of an area of activated nerve cells in response to delivered stimulation, sometimes referred to herein as the "spatial resolution" of the electrical stimulation. The temporal attributes refer to the temporal coding of the electrical stimulation, such as the pulse rate, sometimes referred to herein as the "temporal resolution" of the electrical stimulation. The frequency attributes refer to the frequency analysis of the acoustic input by the filter bank, for example the number and sharpness of the filters in the filter bank, sometimes referred herein as the "frequency resolution" of the electrical stimulation. The instantaneous spectral bandwidth attributes refer to the proportion of the analyzed spectrum that is delivered via electrical stimulation, such as the number of channels stimulated out of the total number of channels in each stimulation frame.

The spatial resolution of electrical stimulation may be controlled, for example, through the use of different electrode configurations for a given stimulation channel to activate nerve cell regions of different widths. Monopolar stimulation, for instance, is an electrode configuration where for a given stimulation channel the current is "sourced" via one of the intra-cochlea electrodes 128, but the current is "sunk" by an electrode outside of the cochlea, sometimes referred to as the extra-cochlear electrode (ECE) 139 (FIGS. 1A and 1B). Monopolar stimulation typically exhibits a large degree of current spread (i.e., wide stimulation pattern) and, accordingly, has a low spatial resolution. Other types of electrode configurations, such as bipolar, tripolar, focused multi-polar (FMP), a.k.a. "phased-array" stimulation, etc. typically reduce the size of an excited neural population by "sourcing" the current via one or more of the intra-cochlear electrodes 128, while also "sinking" the current via one or more other proximate intra-cochlear electrodes. Bipolar, tripolar, focused multi-polar and other types of electrode configurations that both source and sink current via intra-cochlear electrodes are generally and collectively referred to herein as "focused" stimulation. Focused stimulation typically exhibits a smaller degree of current spread (i.e., narrow stimulation pattern) when compared to monopolar stimulation and, accordingly, has a higher spatial resolution than monopolar stimulation. Likewise, other types of electrode configurations, such as double electrode mode, virtual channels, wide channels, defocused multi-polar, etc. typically increase the size of an excited neural population by "sourcing" the current via multiple neighboring intra-cochlear electrodes.

The cochlea is tonotopically mapped, that is, partitioned into regions each responsive to sound signals in a particular frequency range. In general, the basal region of the cochlea is responsive to higher frequency sounds, while the more apical regions of the cochlea are responsive to lower frequencies. The tonopotic nature of the cochlea is leveraged in cochlear implants such that specific acoustic frequencies are allocated to the electrodes 128 of the stimulating assembly 118 that are positioned close to the corresponding tonotopic region of the cochlea (i.e., the region of the cochlea that would naturally be stimulated in acoustic hearing by the acoustic frequency). That is, in a cochlear implant, specific frequency bands are each mapped to a set of one or more electrodes that are used to stimulate a selected (target) population of cochlea nerve cells. The frequency bands and associated electrodes form a stimulation channel that delivers stimulation signals to the recipient.

In general, it is desirable for a stimulation channel to stimulate only a narrow region of neurons such that the resulting neural responses from neighboring stimulation channels have minimal overlap. Accordingly, the ideal stimulation strategy in a cochlear implant would use focused stimulation channels to evoke perception of all sound signals at any given time. Such a strategy would, ideally, enable each stimulation channel to stimulate a discrete tonotopic region of the cochlea to better mimic natural hearing and enable better perception of the details of the sound signals. The present inventor has realized that, although focused stimulation generally improves hearing performance, this improved hearing performance comes at the cost of significant increased power consumption, added delays to the processing path, and increased complexity, etc. relative to the use of only monopolar stimulation. Additionally, the present inventor has realized that not all listening situations benefit from the increased fidelity offered by focused stimulation as different listening situations present varying levels of difficulty to cochlear implant recipients. For example, understanding speech in a quiet room is easier than understanding the same speech in a busy restaurant with many competing speakers. Accordingly, the present inventor has realized that recipients benefit more or less from the details of sound presented using increased stimulus resolution in different environments.

In accordance with the embodiments presented herein, a hearing prosthesis is configured to analyze received sound signals to determine the primary or main sound "class" of the sound signals. In general, the sound class provides an indication of the difficulty/complexity of a recipient's listening situation/environment (i.e., the environment in which the prosthesis is currently/presently located). Based on the sound class of the sound signals, the hearing prosthesis is configured to set the stimulus resolution of the electrical stimulation signals that are delivered to the recipient to evoke perception of the sound signals. The stimulus resolution is set in a manner that optimizes the tradeoff between hearing performance (e.g., increased fidelity) and power consumption (e.g., battery life). The hearing prosthesis uses higher resolution stimulation (i.e., stimulation that provides relatively more acoustic detail) in more challenging listening situations with increased expected listening effort, and uses lower resolution stimulation (i.e., stimulation that provides relatively less acoustic detail) in easier listening situations with lower expected listening effort. Since there is limited power available in a cochlear implant, it is therefore advantageous to adapt the stimulation resolution depending on the listening situation in order to optimize the stimulus resolution for the best overall hearing performance within the long-term power budget.

In accordance with the embodiments presented herein, the spatial resolution (i.e., the spatial attributes of the electrical stimulation) can be increased, for example, through use of focused stimulation. Conversely, the spatial resolution can be lowered, for example, through the use of monopolar, or wide/defocused, stimulation. These decreases in the stimulation resolution have the benefit of lower power consumption and lower complexity, but they also sacrifice listening fidelity (e.g., loss of sound details). In addition, the temporal resolution (i.e., the temporal attributes of the electrical stimulation) can be varied, for example, by changing the rate of the current pulses forming the electrical stimulation. Higher pulse rates offer higher temporal resolution and use more power, while lower pulse rates offer lower temporal resolution and are more power efficient.

Consequently, the stimulus resolution can be varied with differing associated power costs and, in certain situations, the techniques presented herein purposely downgrade hearing performance (e.g., speech perception) to reduce power consumption. However, this downgrade in hearing performance is dynamically activated only in listening situations where the recipient likely does not have difficulty understanding/perceiving the sound signals with lower stimulus resolution (e.g., monopolar stimulation, defocused stimulation, etc.) and/or does not need the details provided by high resolution (e.g., focused stimulation).

Figure 3:
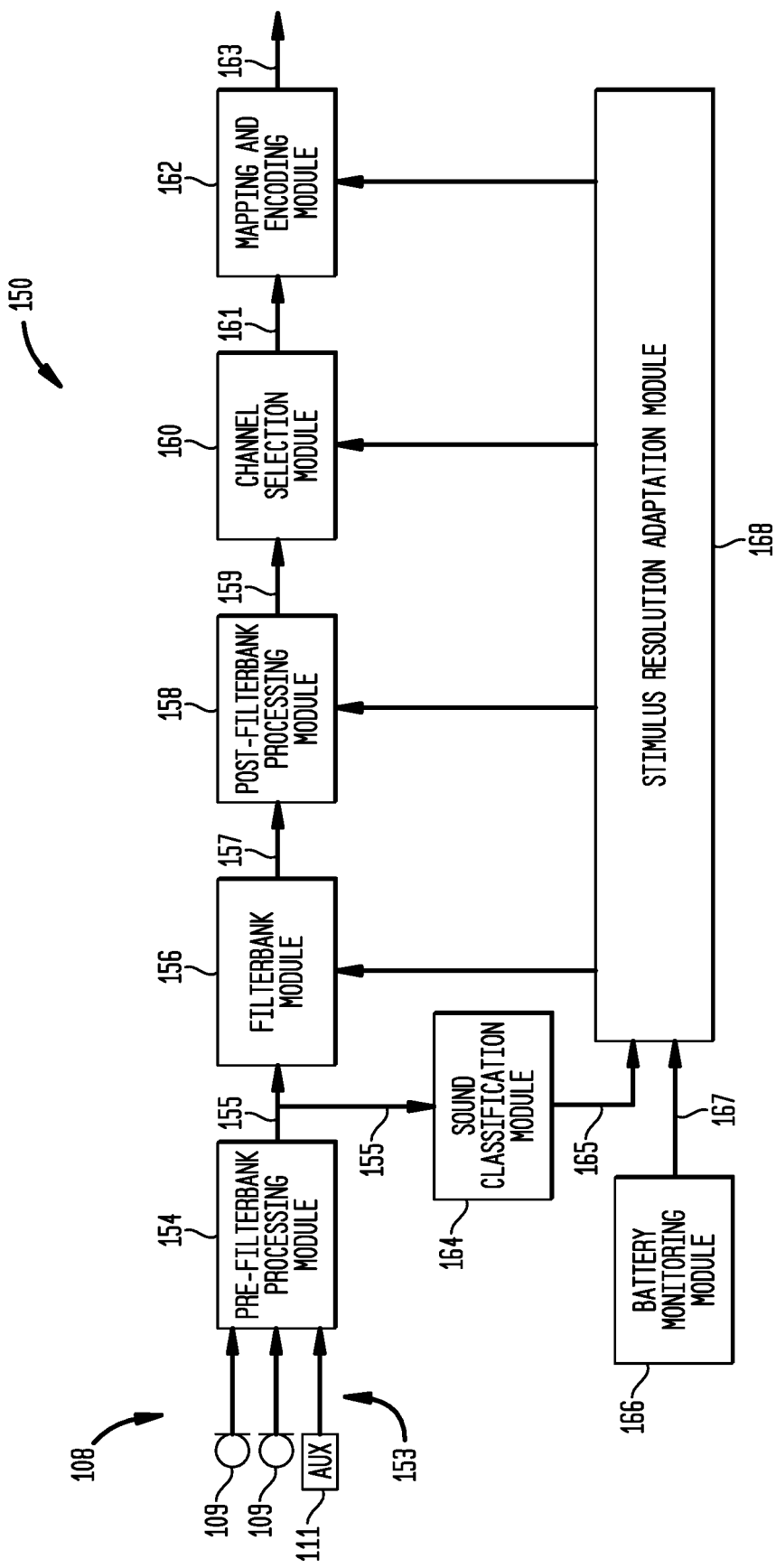
FIG. 3 is a functional block diagram illustrating a hearing prosthesis accordance with embodiments presented herein.

FIG. 3 is a schematic diagram illustrating the general signal processing path 150 of a cochlear implant, such as cochlear implant 100, in accordance with embodiments presented herein. As noted, the cochlear implant 100 comprises one or more sound input elements 108. In the example of FIG. 3, the sound input elements 108 comprise two microphones 109 and at least one auxiliary input 111 (e.g., an audio input port, a cable port, a telecoil, a wireless transceiver, etc.). If not already in an electrical form, sound input elements 108 convert received/input sound signals into electrical signals 153, referred to herein as electrical input signals, that represent the received sound signals. As shown in FIG. 3, the electrical input signals 153 are provided to a pre-filterbank processing module 154.

The pre-filterbank processing module 154 is configured to, as needed, combine the electrical input signals 153 received from the sound input elements 108 and prepare those signals for subsequent processing. The pre-filterbank processing module 154 then generates a pre-filtered output signal 155 that, as described further below, is the basis of further processing operations. The pre-filtered output signal 155 represents the collective sound signals received at the sound input elements 108 at a given point in time.

The cochlear implant 100 is generally configured to execute sound processing and coding to convert the pre-filtered output signal 155 into output signals that represent electrical stimulation for delivery to the recipient. As such, the sound processing path 150 comprises a filterbank module (filterbank) 156, a post-filterbank processing module 158, a channel selection module 160, and a channel mapping and encoding module 162.

In operation, the pre-filtered output signal 155 generated by the pre-filterbank processing module 154 is provided to the filterbank module 156. The filterbank module 156 generates a suitable set of bandwidth limited channels, or frequency bins, that each includes a spectral component of the received sound signals. That is, the filterbank module 156 comprises a plurality of band-pass filters that separate the pre-filtered output signal 155 into multiple components/channels, each one carrying a single frequency sub-band of the original signal (i.e., frequency components of the received sounds signal).

The channels created by the filterbank module 156 are sometimes referred to herein as sound processing channels, and the sound signal components within each of the sound processing channels are sometimes referred to herein as band-pass filtered signals or channelized signals. The band-pass filtered or channelized signals created by the filterbank module 156 are processed (e.g., modified/adjusted) as they pass through the sound processing path 150. As such, the band-pass filtered or channelized signals are referred to differently at different stages of the sound processing path 150. However, it will be appreciated that reference herein to a band-pass filtered signal or a channelized signal may refer to the spectral component of the received sound signals at any point within the sound processing path 150 (e.g., pre-processed, processed, selected, etc.).

At the output of the filterbank module 156, the channelized signals are initially referred to herein as pre-processed signals 157. The number 'm' of channels and pre-processed signals 157 generated by the filterbank module 156 may depend on a number of different factors including, but not limited to, implant design, number of active electrodes, coding strategy, and/or recipient preference(s). In certain arrangements, twenty-two (22) channelized signals are created and the sound processing path 150 is said to include 22 channels.

The pre-processed signals 157 are provided to the post-filterbank processing module 158. The post-filterbank processing module 158 is configured to perform a number of sound processing operations on the pre-processed signals 157. These sound processing operations include, for example, channelized gain adjustments for hearing loss compensation (e.g., gain adjustments to one or more discrete frequency ranges of the sound signals), noise reduction operations, speech enhancement operations, etc., in one or more of the channels. After performing the sound processing operations, the post-filterbank processing module 158 outputs a plurality of processed channelized signals 159.

In the specific arrangement of FIG. 3, the sound processing path 150 includes a channel selection module 160. The channel selection module 160 is configured to perform a channel selection process to select, according to one or more selection rules, which of the 'm' channels should be use in hearing compensation. The signals selected at channel selection module 160 are represented in FIG. 3 by arrow 161 and are referred to herein as selected channelized signals or, more simply, selected signals.

In the embodiment of FIG. 3, the channel selection module 156 selects a subset 'n' of the 'm' processed channelized signals 159 for use in generation of electrical stimulation for delivery to a recipient (i.e., the sound processing channels are reduced from 'm' channels to 'n' channels). In one specific example, the 'n' largest amplitude channels (maxima) from the 'm' available combined channel signals/masker signals is made, with 'm' and 'n' being programmable during initial fitting, and/or operation of the prosthesis. It is to be appreciated that different channel selection methods could be used, and are not limited to maxima selection.

It is also to be appreciated that, in certain embodiments, the channel selection module 160 may be omitted. For example, certain arrangements may use a continuous interleaved sampling (CIS), CIS-based, or other non-channel selection sound coding strategy.

The sound processing path 150 also comprises the channel mapping module 162. The channel mapping module 162 is configured to map the amplitudes of the selected signals 161 (or the processed channelized signals 159 in embodiments that do not include channel selection) into a set of output signals (e.g., stimulation commands) that represent the attributes of the electrical stimulation signals that are to be delivered to the recipient so as to evoke perception of at least a portion of the received sound signals. This channel mapping may include, for example, threshold and comfort level mapping, dynamic range adjustments (e.g., compression), volume adjustments, etc., and may encompass selection of various sequential and/or simultaneous stimulation strategies.

In the embodiment of FIG. 3, the set of stimulation commands that represent the electrical stimulation signals are encoded for transcutaneous transmission (e.g., via an RF link) to an implantable component 104 (FIGS. 1A and 1B). This encoding is performed, in the specific example of FIG. 3, at the channel mapping module 162. As such, channel mapping module 162 is sometimes referred to herein as a channel mapping and encoding module and operates as an output block configured to convert the plurality of channelized signals into a plurality of output signals 163.

Also shown in FIG. 3 are a sound classification module 164, a battery monitoring module 166, and a stimulus resolution adaption module 167. The sound classification module 164 is configured to evaluate/analyze the input sound signals and determine the sound class of the sound signals. That is, the sound classification module 164 is configured to use the received sound signals to "classify" the ambient sound environment and/or the sound signals into one or more sound categories (i.e., determine the input signal type). The sound classes/categories may include, but are not limited to, "Speech," "Noise," "Speech+Noise," "Music," and "Quiet." As described further below, the sound classification module 164 may also estimate the signal-to-noise ratio (SNR) of the sound signals. In one example, the operations of the sound classification module 164 are performed using the pre-filtered output signal 155 generated by the pre-filterbank processing module 154.

The sound classification module 164 generates sound classification information/data 165 that is provided to the stimulus resolution adaptation module 168. The sound classification data 165 represents the sound class of the sound signals and, in certain examples, the SNR of the sound signals. Based on the sound classification data 165, the stimulus resolution adaptation module 168 is configured to determine a level of stimulus resolution that should be used in delivering electrical stimulation signals to represent (evoke perception of) the sound signals. The level of stimulus resolution that should be used in delivering electrical stimulation signals is sometimes referred to herein as the "target" stimulus resolution.

The stimulus resolution adaptation module 168 is configured to adjust one or more operations performed in the sound processing path 150 so as to achieve the target stimulus resolution (i.e., adapt the resolution of the electrical stimulation that is delivered to the recipient). The stimulus resolution adaptation module 168 may adjust operations of the filterbank module 156, the post-filterbank processing module 158, the channel selection module 160, and/or the mapping and encoding module 162 to generate output signals representative of electrical stimulation signals having the target stimulus resolution.

The stimulus resolution adaptation module 168 may adjust operations of the sound processing path 150 at a number of different time scales. For example, the stimulus resolution adaptation module 168 may determine the target stimulus resolution and make corresponding processing adjusts in response to a triggering event, such as the detection of a change in the listening environment (e.g., when the sound classification data 165 indicates the cochlear implant 100 is in a listening environment that is different from the previous listening environment). Alternatively, the stimulus resolution adaptation module 168 can determine the target stimulus resolution and make corresponding processing adjusts substantially continuously, periodically (e.g., every 1 second, every 5 seconds, etc.,), etc.

FIG. 3 illustrates an arrangement in which the cochlear implant 100 also comprises a battery monitoring module 166. The battery monitoring module 166 is configured to monitor the charge status of the battery/batteries (e.g., monitor charge level, remaining battery life, etc.) and provide battery information 167 to the stimulus resolution adaptation module 168. In addition to the sound classification data 165, the stimulus resolution adaptation module 168 may also use the battery information 167 to determine the target stimulus resolution and make corresponding processing adjusts to the sound processing path operations. For example, if the battery information 167 indicates that the cochlear implant battery/batteries are below a threshold charge level (e.g., below 20% charge), the stimulus resolution adaptation module 168 can switch the sound processing path 150 to a power saving mode that uses lower resolution (e.g., monopolar stimulation or defocused stimulation only) to conserve power.

FIG. 3 also illustrates a specific arrangement that includes one sound classification module 164. It is to be appreciated that alternative embodiments may make use of multiple sound classification modules. In such embodiments, the stimulus resolution adaption module 168 is configured to utilize the information from each of the multiple sound classification modules to determine a target stimulus resolution and adapt the sound processing operations accordingly (i.e., so that the resulting stimulation has a resolution that corresponds to the target stimulus resolution).

Although FIG. 3 illustrates a cochlear implant arrangement, it is to be appreciated that the embodiments presented herein may also be implemented in other types of hearing prosthesis. For example, the techniques presented herein may be used in electro-acoustic hearing prostheses that are configured to deliver both acoustical stimulation and electrical stimulation to a recipient. In such embodiments, the prosthesis would include two parallel sound processing paths, where the first sound processing path is an electric sound processing path (cochlear implant sound processing path) similar to that is shown in FIG. 3. In such arrangements, the second sound processing path is an acoustic sound processing path (hearing aid sound processing path) that is configured to generate output signals for use in acoustically stimulating the recipient.

Figure 4:
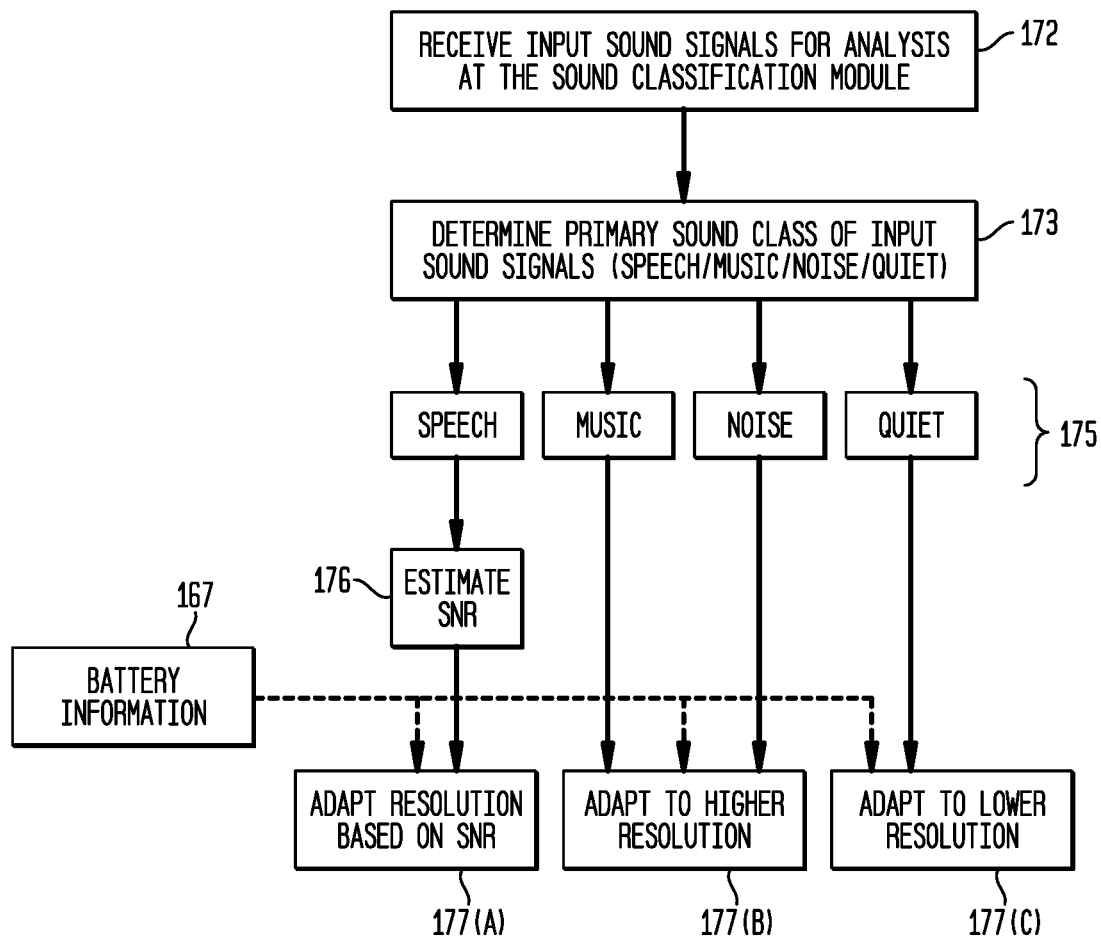
FIG. 4 is a flow diagram in accordance with embodiments presented herein.

FIG. 4 is a flow diagram illustrating further details of the techniques presented herein. For ease of illustration, FIG. 4 will be described with reference to the arrangement of FIG. 3.

The flow of FIG. 4 begins at 172 where the cochlear implant 100 receives input sound signals for analysis by the sound classification module 164. At 173, the sound classification module 164 determines the sound class of the input sound signals. FIG. 4 illustrates example sound classes 175 that include: "Speech," "Music," "Noise," and "Quiet." However, it is to be appreciated that additional sound classes are also possible.

In the example of FIG. 4, the stimulus resolution adaption module 168 is configured to adapt the sound processing path 150 differently depending on the determined sound class. The different adaptions are generally shown in FIG. 4 at blocks 177(A), 177(B), and 177(C). More specifically, FIG. 4 illustrates that for the "Music" and "Noise" sound classes, a higher target stimulus resolution is preferred since these are more difficult listening situations for a recipient. Accordingly, at 177(B), the stimulus resolution adaption module 168 implements one or more adjustments to the sound processing path 150 to set a higher target resolution for the electrical stimulation delivered to the recipient. For the "Quiet" sound class, at 176(C) the stimulus resolution adaption module 168 implements one or more adjustments to the sound processing path 150 to set a lower target stimulus resolution.

For the "Speech" sound class, a signal-to-noise ratio (SNR) of the input sound signals is used to control the resolution. The SNR provides a measure of how much speech compared to noise is present in the input sound signals. Therefore, at 176, the SNR of the input sound signals is estimated and, at 176(A) the SNR is used to determine the target stimulus resolution. In general, the higher the SNR, the lower the target stimulus resolution and, conversely, the lower the SNR, the higher the target stimulus resolution. The SNR can be used to select one of a number of discrete stimulation resolution levels, or could be applied across a continuum. For example, in one embodiment, the stimulus resolution adaption module 168 uses only two (2) stimulus resolution levels for the "Speech" sound class. These two levels comprise a low resolution setting for SNRs greater than a certain threshold (e.g., greater than 10 dB) where speech is much stronger than the noise, and a high resolution setting for SNRs below the threshold (e.g., below 10 dB). In other embodiments, the stimulus resolution adaption module 168 may make use of a large number of different resolution levels that each correlate to different SNR ranges. In these embodiments, the determined SNR is mapped to one of the number of different ranges and, accordingly, used to select the corresponding stimulus resolution.

Also shown in FIG. 4 is the battery information 167 which may be an optional input to the resolution adaptation blocks 177(A)-177(C). As noted, the battery information 167 represents the state of charge of the battery/batteries and can be used to modify the target resolutions at 177(A)-177(C). For example, if the battery charge is low, for example below 20%, then a target higher resolution at 177(A) or 177(B) might be lowered so that battery life is given more priority. The battery information 167 could also be used to modify the SNR threshold(s) for the speech class. For example, in a low battery situation (e.g., charge below a threshold level), the SNR threshold(s) for selecting between two resolution steps could also be lowered, for example from 10 dB to 5 dB, to favor the use of lower resolution and, accordingly, conserve power.

Figure 5A:
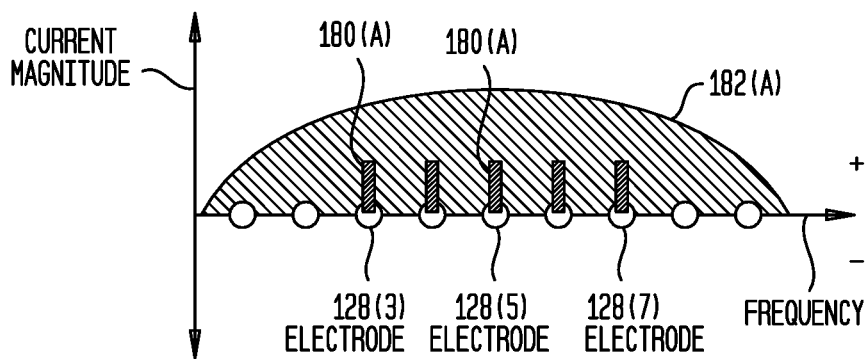
FIGS. 5A, 5B, 5C, 5D, and 5E are schematic diagrams illustrating the spatial resolution of electrical stimulation signals in accordance with embodiments presented herein.
Figure 5B:
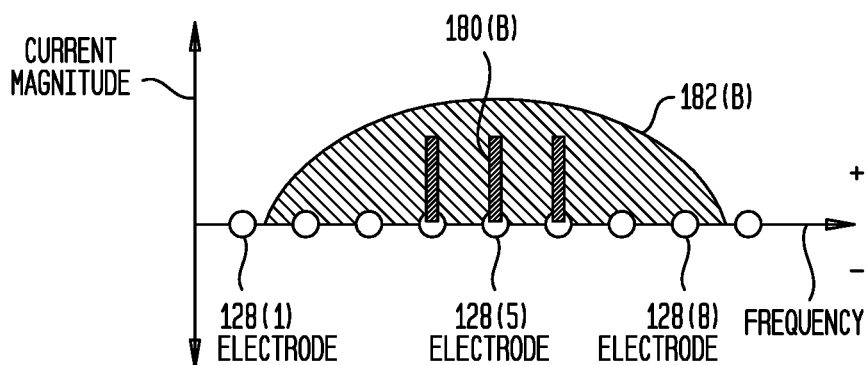
Figure 5C:
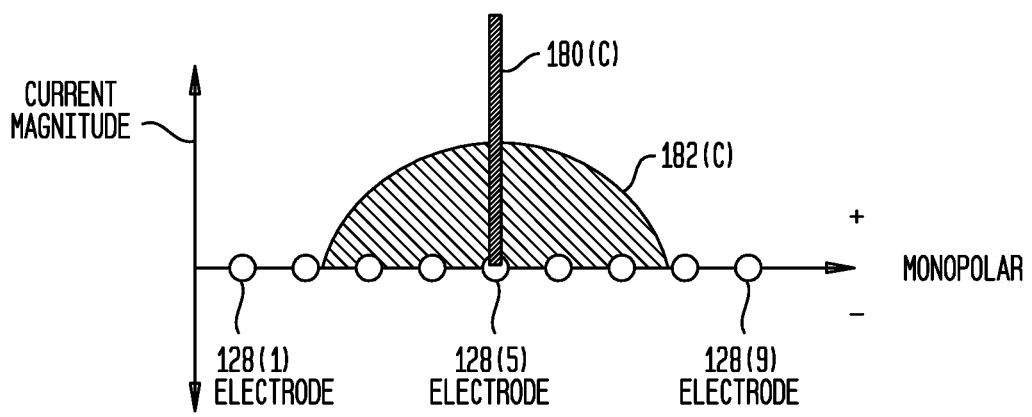

As described elsewhere herein, the stimulus resolution adaption module 168 may set or adjust various operations of the sound processing path 150, such as the operations of the filterbank module 156, the post-filterbank processing module 158, the channel selection module 160, and/or the mapping and encoding module 162, to set the stimulus resolution of the delivered electrical stimulation signals. In one embodiment, the spatial/spectral attributes of the stimulus resolution are set by switching between different channel/electrode configurations, such as between monopolar stimulation, wide/defocused stimulation, focused (e.g., multipolar current focusing) stimulation, etc. FIGS. 5A-5E are a series of schematic diagrams illustrating exemplary electrode currents and stimulation patterns for five (5) different channel configurations. It is to be appreciated that the stimulation patterns shown in FIGS. 5A-5C are generally illustrative and that, in practice, the stimulation current may spread differently in different recipients.

Each of the FIGS. 5A-5E illustrates a plurality of electrodes shown as electrodes 128(1)-128(9), which are spaced along the recipient's cochlea frequency axis (i.e., along the basilar membrane). FIGS. 5A-5E also include solid lines of varying lengths that extend from various electrodes to generally illustrate the intra-cochlear stimulation current 180(A)-180(E) delivered in accordance with a particular channel configuration. However, it is to be appreciated that stimulation is delivered to a recipient using charge-balanced waveforms, such as biphasic current pulses and that the length of the solid lines extending from the electrodes in each of FIGS. 5A-5E illustrates the relative "weights" that are applied to both phases of the charge-balanced waveform at the corresponding electrode in accordance with different channel configurations. As described further below, the different stimulation currents 180(A)-180(E) (i.e., different channel weightings) results in different stimulation patterns 182(A)-182(E), respectively, of voltage and neural excitation along the frequency axis of the cochlea Referring first to FIG. 5C, shown is the use of a monopolar channel configuration where all of the intra-cochlear stimulation current 180(C) is delivered with the same polarity via a single electrode 128(5). In this embodiment, the stimulation current 180(C) is sunk by an extra-cochlear return contact which, for ease of illustration, has been omitted from FIG. 5C. The intra-cochlear stimulation current 180(C) generates a stimulation pattern 182(C) which, as shown, spreads across neighboring electrodes 128(3), 128 (4), 128(6), and 128(7). The stimulation pattern 182(C) represents the spatial attributes (spatial resolution) of the monopolar channel configuration.

FIGS. 5A and 5B illustrate wide or defocused channel configurations where the stimulation current is split amongst an increasing number of intracochlear electrodes and, accordingly, the width of the stimulation patterns increases and thus provide increasingly lower spatial resolutions. In these embodiments, the stimulation current 180(A) and 180(B) is again sunk by an extra-cochlear return contact which, for ease of illustration, has been omitted from FIGS. 5A and 5B.

More specifically, in FIG. 5B the stimulation current 180(B) is delivered via three electrodes, namely electrodes 128(4), 128(5), and 128(6). The intra-cochlear stimulation current 180(B) generates a stimulation pattern 182(B) which, as shown, spreads across electrodes 128(2)-128(8). In FIG. 5A, the stimulation current 180(A) is delivered via five electrodes, namely electrodes 128(3)-128(7). The intra-cochlear stimulation current 180(A) generates a stimulation pattern 182(A) which, as shown, spreads across electrodes 128(1)-128(9). In general, the wider the stimulation pattern, the lower the spatial resolution of the stimulation signals.

Figure 5D:
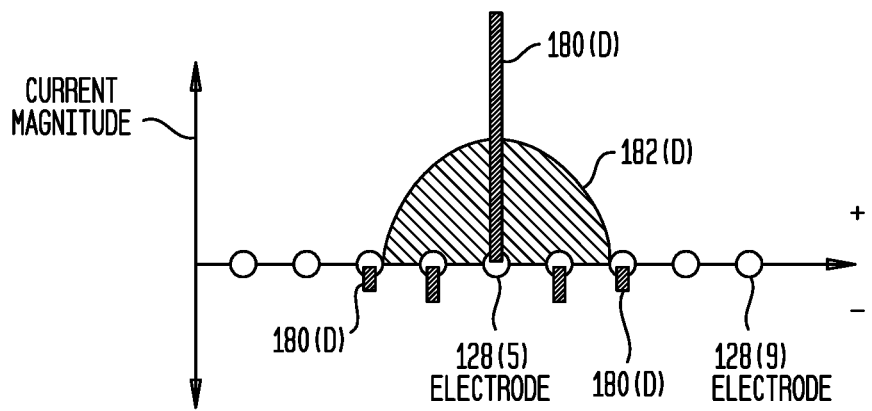
Figure 5E:
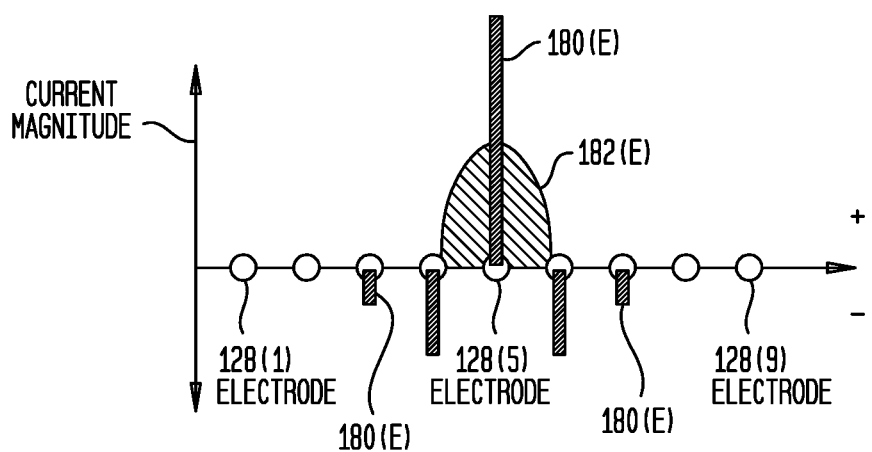

FIGS. 5D and 5E illustrate focused channel configurations where intracochlear compensation currents are added to decrease the spread of current along the frequency axis of the cochlea. The compensation currents are delivered with a polarity that is opposite to that of a primary/main current. In general the more compensation current at nearby electrodes, the more focused the resulting stimulation pattern (i.e., the lower the width of the stimulus patterns increase and thus increasingly higher spatial resolutions). That is, the spatial resolution is increased by introducing increasing large compensation currents on electrodes surrounding the central electrode with the positive current.

More specifically, in FIG. 5D positive stimulation current 180(D) is delivered via electrode 128(5) and stimulation current 180(D) of opposite polarity is delivered via the neighboring electrodes, namely electrodes 128(3), 128(4), 128(6), and 128(7). The intra-cochlear stimulation current 180(D) generates a stimulation pattern 182(D) which, as shown, only spreads across electrodes 128(4)-128(6). In FIG. 5E, positive stimulation current 180(E) is delivered via electrode 128(5), while stimulation current 180(E) of opposite polarity is delivered via the neighboring electrodes, namely electrodes 128(3), 128(4), 128(6), and 128(7). The intra-cochlear stimulation current 180(E) generates a stimulation pattern 182(E) which, as shown, is generally localized to the spatial area adjacent electrode 128(5).

The difference in the stimulation patterns 182(D) and 182(E) in FIGS. 5D and 5E, respectively, is due to the magnitudes (i.e., weighting) of opposite polarity current delivered via the neighboring electrodes 128(3), 128(4), 128(6), and 128(7). In particular, FIG. 5D illustrates a partially focused configuration where the compensation currents do not fully cancel out the main current on the central electrode and the remaining current goes to a far-field extracochlear electrode (not shown). FIG. 5E is a fully focused configuration where the compensation currents fully cancel out the main current on the central electrode 128(5) (i.e., no far-field extracochlear electrode is needed).

As noted, FIGS. 5A-5E collectively illustrate techniques for adjusting the spatial resolution (i.e., adjusting the spatial attributes of the electrical stimulation) in accordance with embodiments presented herein. However, also as noted, it is to be appreciated that other methods for altering the stimulus resolution could be used in combination with, or as an alternative to, adjustments to the spatial resolution enabled by different stimulation strategies. For example, another technique for adapting the stimulus resolution includes varying the temporal resolution via pulse rate (i.e., higher pulse rates for higher temporal resolutions and lower pulse rates for lower temporal resolutions). In general, changes to the temporal resolution may be implemented in the post-filter bank processing module 158 (e.g., during calculation of the channel envelope signals) and/or in the mapping and encoding module 162 (e.g., selection of the pulse rate).

Another technique for adapting the stimulus resolution includes varying the instantaneous spectral bandwidth of the stimulation by changing the number of maxima in the channel selection. For example, the instantaneous bandwidth can be increased by increasing the number of channels selected by the channel selection module 160 and decreased by decreasing the number of channels selected by the channel selection module 160.

A still other technique for adapting the stimulus resolution includes varying the frequency resolution. The frequency resolution of the filterbank module 156 can be increased by, for example, in an FFT filterbank using a higher-point FFT. The frequency resolution of the filterbank module 156 can be decreased by, for example in an FFT filterbank using a lower-point FFT.

Shown below is a table (Table 1) illustrating different types of stimulus attributes and associated resolution adaptions in accordance with embodiments presented herein.

TABLE 1

| Stimulation Attribute | Resolution Adaption |
| --- | --- |
| Spatial | Decrease resolution by multipolar defocusing (split stimulation across multiple electrodes) |
| Spatial | Increase resolution by multipolar focusing. Use compensating currents of the opposite polarity to minimize current spread from main current from central electrode |
| Spatial | Decrease resolution by using parallel stimulation strategies: highest resolution with fully sequential stimulation of each channel, resolution is lowered by first stimulating pairs of channels and further lowered by stimulation more than two channels in parallel |
| Temporal | Decrease resolution by lowering the pulse rate for each channel |
| Temporal | Increase resolution by increase the pulse rate for each channel |
| Instantaneous spectral bandwidth | Increase instantaneous spectral bandwidth by increasing the number of channels selected during each stimulation frame |
| Instantaneous spectral bandwidth | Decrease instantaneous spectral bandwidth by decreasing the number of channels selected during each stimulation frame |
| Frequency | Increase frequency resolution of filterbank |
| Frequency | Decrease frequency resolution of filterbank |

The embodiments presented herein have been primarily described with respect to the use of the sound class as the mechanism for determining a target stimulus resolution. It is to be appreciated that other techniques for determining the target stimulus resolution may be used in accordance with embodiments presented herein. For example, a direct measure of the degree of listening difficulty (listening effort) could be used to determine the target stimulus resolution. The listening effort may be determined, for example, using electroencephalography (EEG) (i.e., an electrophysiological monitoring method to record electrical activity of the brain), pupil dilation, or a physiological measure of stress (e.g., blood pressure, cortisol level, etc.). In these embodiments, if the listening effort is determined to be relatively high (with reference to a baseline), then the resolution can be increased. Conversely, if the listening effort is determined to be relatively low (with reference to a baseline), then the resolution can be decreased.

Figure 6:
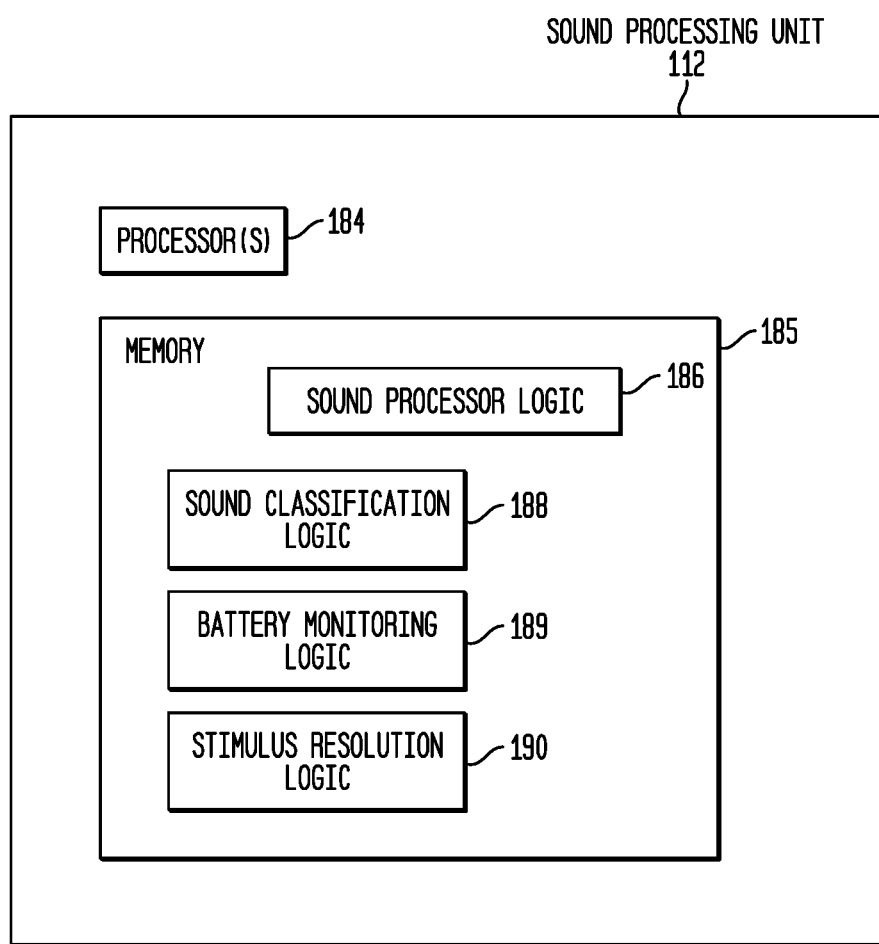
FIG. 6 is a block diagram of a sound processing unit in accordance with embodiments presented herein.

In a further embodiment, the target stimulus resolution can be determined based on a direct input from the recipient. The input may indicate the recipient's listening effort or directly indicate a desired stimulus resolution. In certain such embodiments, the system could be trained so as to, over time, automatically adjust stimulus resolution based on previously received recipient inputs. For example, the hearing prosthesis may be pre-configured with certain thresholds that cause changes between different stimulus resolutions. Over time, the stimulus resolution adaption module can adjust these thresholds using the recipient inputs FIG. 6 is a schematic block diagram illustrating an arrangement for a sound processing unit, such as sound processing unit 112, in accordance with an embodiment of the present invention. As shown, the sound processing unit 112 includes one or more processors 184 and a memory 185. The memory 185 includes sound processor logic 186, sound classification logic 188, battery monitoring logic 189, and stimulus resolution adaption logic 190.

The memory 185 may be read only memory (ROM), random access memory (RAM), or another type of physical/tangible memory storage device. Thus, in general, the memory 185 may comprise one or more tangible (non-transitory) computer readable storage media (e.g., a memory device) encoded with software comprising computer executable instructions and when the software is executed (by the one or more processors 184) it is operable to perform the operations described herein with reference to the sound processor, sound classification module 164, battery monitoring module 166, and stimulus resolution adaption module 168.

FIG. 6 illustrates software implementations for the sound processor, the sound classification module 164, and the stimulus resolution adaption module 168. However, it is to be appreciated that one or more operations associated with the sound processor, the sound classification module 164, the battery monitoring module 166, and the stimulus resolution adaption module 168 may be partially or fully implemented with digital logic gates in one or more application-specific integrated circuits (ASICs).

Merely for ease of illustration, the sound classification module 164 and the stimulus resolution adaption module 168 have been shown and described as elements that are separate from the sound processor. It is to be appreciated that the functionality of the sound classification module 164 and the stimulus resolution adaption module 168 may be incorporated into the sound processor.

FIG. 7 is a flowchart illustrating a method 700 in accordance with embodiments presented herein. Method 700 begins at 702 where a hearing prosthesis receives input sound signals. At 704, the hearing prosthesis determines a sound class of the input sound signals and, at 706, the hearing prosthesis generates, for delivery to a recipient of the hearing prosthesis, electrical stimulation signals that are representative of the input sound signals. At 708, a resolution of the electrical stimulation signals is set based on the sound class of the input sound signals.

FIG. 8 is a flowchart illustrating a method 800 in accordance with embodiments presented herein. Method 800 begins at 802 where a hearing prosthesis located in an acoustic environment receives sound signals. At 804, the hearing prosthesis assesses the acoustic environment based on the sound signals. At 806, the hearing prosthesis generates electrical stimulation representative of the sound signals at a stimulus resolution that is set based on the assessment of the acoustic environment. At 808, the electrical stimulation signals are delivered to a recipient of the hearing prosthesis.

As described in detail above, presented herein are techniques that analyze the acoustic scene/environment of a hearing prosthesis and, accordingly, adjust, adapt, or otherwise set the resolution of electrical stimulation based on the acoustic environment (e.g., based on an estimated listening difficulty that the acoustic environment presents to a recipient of the hearing prosthesis). The techniques presented herein leverage the idea that there are many listening situations that are not difficult for recipients and, in such situations, power should not be wasted to transmit the most accurate neural representation possible. Likewise, in more challenging listening situations that are more taxing for recipients, it may be beneficial to use more power in order to create a more accurate neural activation pattern that lessens the listening burden on the recipient. Accordingly, the techniques presented optimize power consumption and hearing performance based on the listening situation.

It is to be appreciated that the above described embodiments are not mutually exclusive and that the various embodiments can be combined in various manners and arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A device, comprising:
   one or more input elements configured to receive environmental signals;
   at least one battery;
   a classification module configured to classify an ambient environment of the device based on the received environmental signals;
   a battery monitoring module configured to determine a charge level of the at least one battery;
   a processing path configured to convert the environmental signals into one or more output signals for use in delivering stimulation signals to a recipient via one or more stimulation channels; and
   a stimulus resolution adaption module configured to set a degree of current spread associated with stimulation signals delivered via a given stimulation channel based on the classification of the ambient environment and the charge level of the at least one battery.

2. The device of claim 1, wherein the stimulus resolution adaption module is configured to set a degree of current spread associated with stimulation signals delivered via a given stimulation by selecting an electrode configuration for use in delivering the stimulation signals via the given stimulation channel.

3. The device of claim 2, wherein the electrode configuration is a first electrode configuration selected from among a plurality of electrode configurations.

4. The device of claim 1, wherein the one or more input elements include sound input elements configured to receive sound signals, and wherein the classification module is configured to classify an ambient sound environment of the recipient.

5. The device claim 4, wherein the classification module is configured to:
   determine a presence of speech in the sound signals;
   classify the ambient sound environment as speech signals; and
   determine a signal-to-noise ratio of the speech signals.

6. The device of claim 5, wherein the stimulus resolution adaption module is further configured to:
   set a degree of current spread associated with the stimulation signals delivered via the given stimulation channel based on the signal-to-noise ratio of the speech signals.

7. The device of claim 1, wherein the device is a hearing prosthesis.

8. The device of claim 1, wherein the stimulus resolution adaption module is further configured to:
   set a temporal resolution of the stimulation signals based on the based on the classification of the ambient environment and the charge level of the at least one battery.

9. The device of claim 1, further comprising:
   setting a frequency resolution of the stimulation signals based on the classification of the ambient environment and the charge level of the at least one battery.

10. The device of claim 1, wherein to set a degree of current spread associated with stimulation signals delivered via a given stimulation channel based on the classification of the ambient environment and the charge level of the at least one battery, the stimulus resolution adaption module is configured to:
    select a focused electrode channel configuration for delivery of electrical stimulation to the recipient via the one or more stimulation channels.

11. The device of claim 1, wherein to set a degree of current spread associated with stimulation signals delivered via a given stimulation channel based on the classification of the ambient environment and the charge level of the at least one battery, the stimulus resolution adaption module is configured to:
    select from a group of electrode configurations consisting of: monopolar stimulation, bipolar stimulation, multipolar stimulation, and focused multipolar stimulation.

12. A method, comprising:
    receiving environmental signals at one or more input elements of a device comprising at least one battery, a processing path, and a stimulus resolution adaption module;
    determining, with a classification module, a classification of an ambient environment of the device based on the received environmental signals;
    determining, with a battery monitoring module, a charge level of the at least one battery;
    converting, with the processing path, the environmental signals into one or more stimulation signals for delivery to a recipient of the device via one or more stimulation channels; and
    setting, with the stimulus resolution adaption module, a degree of current spread associated with electrical stimulation signals delivered via a given stimulation channel based on the classification of the ambient environment and the charge level of the at least one battery.

13. The method of claim 12, wherein setting a degree of current spread associated with stimulation signals delivered via a given stimulation comprises:
    selecting an electrode configuration for use in delivering the stimulation signals via the given stimulation channel.

14. The method of claim 13, wherein selecting an electrode configuration for use in delivering the electrical stimulation signals to the recipient via the one or more stimulation channels comprises:
    selecting a focused electrode channel configuration for delivery of the electrical stimulation signals to the recipient.

15. The method of claim 13, wherein selecting an electrode configuration for use in delivering the electrical stimulation signals to the recipient via the one or more stimulation channels comprises:
    selecting a defocused electrode channel configuration for delivery of the electrical stimulation signals to the recipient.

16. The method of claim 12, further comprising:
    setting a temporal resolution of the electrical stimulation signals based on the ambient environment of the environmental signals and the charge level of the at least one battery.

17. The method of claim 12, further comprising:
    setting a frequency resolution of the electrical stimulation signals based on the ambient environment of the input environmental signals the charge level of the at least one battery.

18. The method of claim 12, further comprising:
setting an instantaneous spectral bandwidth of the electrical stimulation signals by changing the number of selected channels in a channel selection process based on the ambient environment of the environmental signals the charge level of the at least one battery.

19. The method of claim 12, wherein the one or more input elements include sound input elements configured to receive sound signals, and wherein determining a classification of an ambient environment comprises:
determining a sound classification of the ambient environment of the recipient.

20. The method of claim 19, wherein determining a sound classification of an ambient environment comprises:
determining the presence of speech in the sound signals; and
classifying the ambient sound environment as speech.

* * * * *